United States Patent [19]

Hildebrand

[11] 4,037,327

[45] July 26, 1977

[54] DOG HEIGHT MEASURING WICKET

[76] Inventor: George Hildebrand, 843-a Heritage Village, Southbury, Conn. 06488

[21] Appl. No.: 667,412

[22] Filed: Mar. 16, 1976

Related U.S. Application Data

[63] Continuation-in-part of Ser. No. 538,412, Jan. 3, 1975, Pat. No. 3,943,630.

[51] Int. Cl.² .......................... G01B 5/00; G01B 5/02
[52] U.S. Cl. ................................. 33/169 R; 33/174 D
[58] Field of Search .............. 33/168 B, 169 R, 174 D

[56] References Cited

U.S. PATENT DOCUMENTS

| 325,134 | 8/1885 | Wainwright | 33/169 R |
|---|---|---|---|
| 721,800 | 3/1903 | Heatly | 33/169 R |
| 1,457,964 | 6/1923 | Doty | 33/169 R |
| D. 177,541 | 4/1956 | Wambach, Jr. | 33/169 R |

FOREIGN PATENT DOCUMENTS 2,016,905  10/1971  Germany ........................ 33/174 D Primary Examiner—Richard E. Aegerter
Assistant Examiner—Richard R. Stearns
Attorney, Agent, or Firm—Kenneth S. Goldfarb

[57] ABSTRACT

A measuring wicket for dogs comprising a U-shaped member having a pair of spaced tubular legs and an interconnecting bar. A cross bar extends between the legs below the interconnecting bar. Each of said legs has an enlarged boss at the bottom thereof. There are grooves in leg extensions telescopically mounted in said legs and latching means in said bosses which cooperate with the grooves in the leg extensions. The degree of extension is viewed by means of cooperation between the boss and through a particular groove and indicia is provided on the leg to indicate the height of the cross bar.

1 Claim, 3 Drawing Figures

U.S. Patent  July 26, 1977  4,037,327
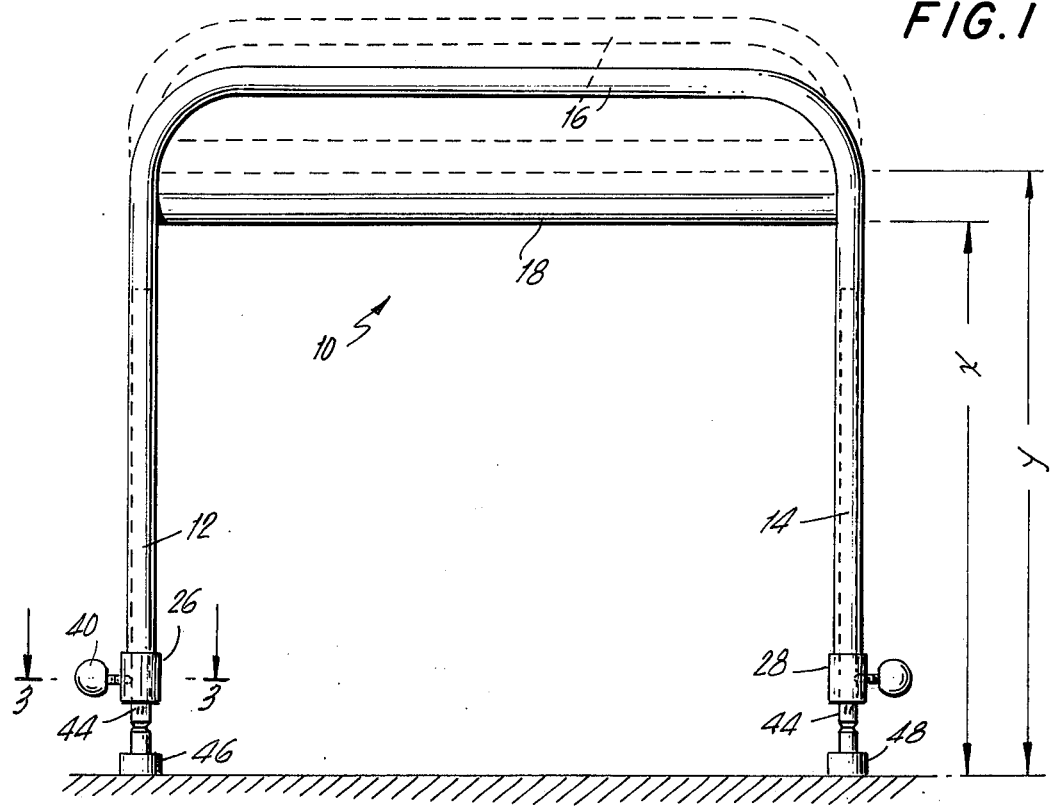
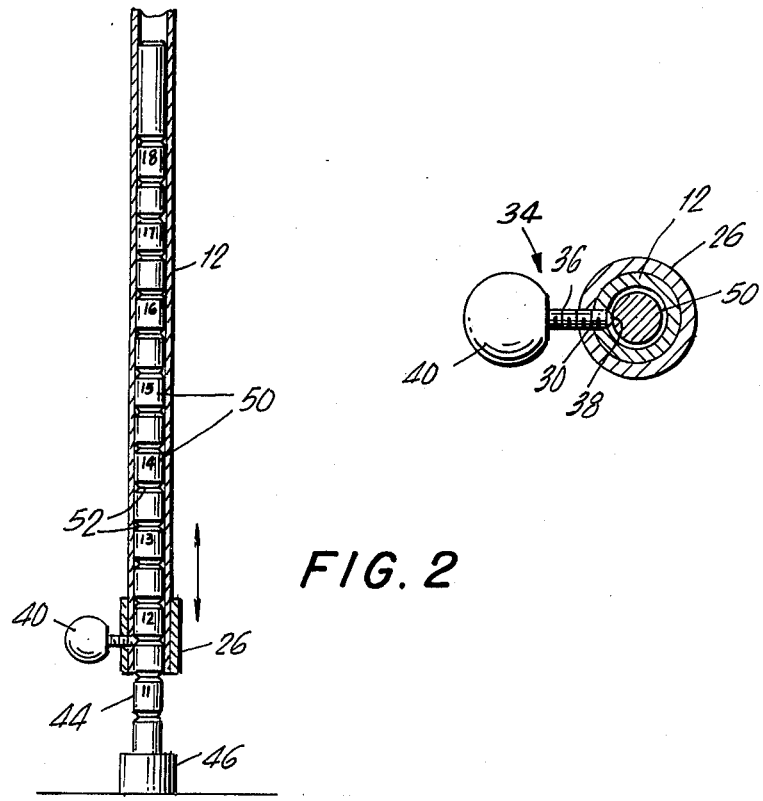

DOG HEIGHT MEASURING WICKET

REFERENCE TO RELATED APPLICATION

This application is a continuation in part of the application of GEORGE HILDEBRAND Ser. No. 538,412 now U.S. Pat. No. 3,943,630 for MEASURING WICKET FOR HEIGHT OF DOGS.

BACKGROUND OF THE INVENTION

1. Field of the Invention

This invention relates to the class of measuring instruments and more particularly to a wicket for measuring the height of a dog.

2. Description of the Prior Art

At dog shows, in those breeds where certain heights are specified in the standard for the particular breed as disqualifications or in any class where the conditions include a height specification, the dog show judge may be required to make a determination as to whether any dog measures within the specified limits. In the past, various types of equipment have been used which have resulted in considerable difficulties in providing for an accurate determination of the height of the dog. This is because it is often difficult to cause the dog under consideration to stand in an erect manner for a period long enough for the accurate measurement using rulers, tape measures, or the like, to be employed.

The problem presented is to provide a device which in a positive manner will assure accurate measurement in a very short time and with the dog shifting in the position of its shoulders and the like so that a reading of less than the dog's actual height cannot be made because the dog is incorrectly positioned during the measurement.

In the previously filed application, Ser. No. 538,412 the legs were provided with a series of openings therein. These openings, together with their corresponding function are eliminated and in lieu thereof indicia is provided on the leg extensions.

SUMMARY OF THE INVENTION

The present invention conceives of a wicket which is placed across the dogs shoulders in such a manner that if both legs of the wicket touch the ground at all times while the dog is being measured and with the shoulders being shifted, the dog will be considered as being under the particular height for which the wicket is set. The invention conceives of two or three different size adjustable wickets covering all of the various sizes for the various breeds for which height standards have been set and so arranged that the height to which a wicket has been set may be easily ascertained by the judge using the wicket. Each wicket is of U-shape and includes a pair of telescopic legs including tubular leg members, further including a pair of leg extensions provided with a series of spaced notches therein and suitable indicia thereon. Ball detent locking means are provided for conveniently seating the wicket in a predetermined height position. A cross bar for seating on the shoulder of the dog being measured in provided and the space between the top bar of the wicket and the cross bar allows for convenient use of the top bar of the wicket as a handle for placing the wicket on the dog without in any way alarming or discomforting the dog being measured.

It is therefore an object of the invention to provide a measuring wicket for dogs that will enable an individual judge to conveniently and accurately measure the height of a dog thereby eliminating previous difficulties heretofore present in measuring dogs at dog shows and further eliminating the need for measuring committees to obtain accurate measurements.

Still further objects and features of this invention reside in the provision of a measuring wicket for dogs that is simple in construction, inexpensive to manufacture thereby permitting wide use and distribution to dog show holding clubs as to facilitate familiarly with such measuring wickets, which will speed up dog show judging by providing for quicker and more accurate determination of the height of a dog, and which is telescopic in construction, thereby permitting the use of the wicket for a wide variety of heights of dogs.

These, together with the various ancillary objects and features of the present invention, which will become apparent as the following description proceeds, are attained by this measuring wicket for determination of a dog's height, a preferred embodiment of which is illustrated in the accompanying drawings, by way of example, wherein:

BRIEF DESCRIPTION OF THE DRAWING

FIG. 1 is a front elevational view of a measuring wicket constructed in accordance with the concepts of the present invention;

FIG. 2 is an enlarged sectional detail view, illustrating a tubular leg and leg extension; and FIG. 3 is an enlarged sectional view, taken along the plane of line 3—3 in FIG. 1.

DETAILED DESCRIPTION OF THE PREFERRED EMBODIMENT

With continuing reference to the accompanying drawing, wherein like reference numerals designate similar parts throughout the various view, reference numeral 10 is used to generally designate a measuring wicket for dogs constructed in accordance with the concepts of the present invention. The measuring wicket 10 includes a pair of tubular legs 12 and 14 interconnected by an interconnecting bar 16 forming a general U-shaped member. The tubular legs 12 and 14 are also interconnected by a cross bar 18 spaced below and parallel to the interconnecting bar 16. Hence, the space between the interconnecting bar 16 and the cross bar 18 permits the positioning of the hand of the user and upon grasping of the interconnecting bar 16, the entire wicket may be raised, lowered, and positioned over the shoulders of a dog in a convenient fashion. Secured as by welding, brazing, bonding or the like to the legs 12 and 14 are enlarged cylindrical tubular bosses 26 and 28. Each of these bosses 26 and 28 have internally threaded openings 30 therein and a locking means 34 including a set screw 36 provided with a spring pressed ball detent 38 and an enlarged spherical head 40 are provided and are threaded in the opening 30.

A pair of leg extensions 44 are provided having enlarged feet 46 and 48 below the legs. The extensions 44 are telescopically slideable within the legs 12 and 14 and may be selectively locked in an adjustable position through the use of the locking members 34. Measuring indicia 50 are provided on the leg extensions 44 designating the height of the cross bar of the wicket above the ground when a particular pair of grooves 52 in the leg extensions 44 are engaged by the locking means 34. The ball detents 38 are adapted to sit in the grooves 52 and hold the leg extensions in the locked position with the screws 36 threadedly engaged in an inward position. The indicia 50, cooperate with the boss 26 to provide a clear indication as to the height of the wicket 10.

In use, the judge preferably approaching the dog from behind may slip wicket directly over the dog's shoulders and moving the wicket slightly in that area determine if both leg extension feet 46 and 48 rest on the ground. If this is the case, the dog measures under the height to which the wicket has been set. If, with slight movement of the dog or wicket, one of the leg extension feet 46 and 48 are raised, the dog is obviously taller than the height setting of the wicket. The wicket is preferably made in two or three different sizes to accommodate the firth of the animal ranging from a relatively small height for small size or toy breeds, as for example the toy poodle, to very sizeable dogs, such as the Great Dane.

A latitude of modification, substitution and change is intended in the foregoing disclosures, and in some instances some features of the present invention may be employed without a corresponding use of other features.

What is claimed is:

1. A measuring wicket for dogs comprising a U-shaped member having a pair of spaced tubular legs and an interconnecting bar, a cross bar below said interconnecting bar and extending between said legs and secured thereto, leg extensions slidably telescopically received in said legs, enlarged cylindrical bosses at the bottom of said legs, indexing grooves in said extensions co-operable with said cylindrical bosses to indicate the effective height of said cross bar, locking means threadedly mounted in said legs for engagement with said extensions in said grooves selectively locking each of said leg extensions in an adjusted position, each said locking means including a spring pressed ball detent seatable in said grooves, and indicia on said extensions for indicating the height of the cross bar when said locking means is seated in one of said grooves, and enlarged feet on said leg extensions engageable with said bosses when said leg extensions are fully retracted into said legs.

* * * * *